(12) United States Patent
Manhes

(10) Patent No.: US 6,508,827 B1
(45) Date of Patent: *Jan. 21, 2003

(54) INSTRUMENT FOR APPLICATION IN ENDOSCOPIC SURGERY

(75) Inventor: Hubert Manhes, Vichy (FR)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/616,183

(22) Filed: Jul. 14, 2000

Related U.S. Application Data

(63) Continuation of application No. PCT/DE99/00057, filed on Jan. 14, 1999.

(30) Foreign Application Priority Data

Jan. 14, 1998 (DE) .......................................... 198 00 917

(51) Int. Cl.[7] .............................................. A61B 17/28
(52) U.S. Cl. ........................ 606/205; 606/148; 600/104
(58) Field of Search ................................ 606/205, 206, 606/207, 148; 600/564, 104, 153, 154

(56) References Cited

U.S. PATENT DOCUMENTS

| | | | |
|---|---|---|---|
| 5,100,421 A | * 3/1992 | Christoudias | 606/147 |
| 5,234,443 A | 8/1993 | Phan et al. | 606/148 |
| 5,312,391 A | * 5/1994 | Wilk | 606/1 |
| 5,474,057 A | 12/1995 | Makower et al. | 600/214 |
| 5,511,564 A | 4/1996 | Wilk | 128/898 |
| 5,993,467 A | * 11/1999 | Yoon | 606/147 |
| 6,017,358 A | * 1/2000 | Yoon et al. | 606/205 |

FOREIGN PATENT DOCUMENTS

| | | | |
|---|---|---|---|
| DE | 4324254 | * | 1/1995 |
| DE | 196 27 992 A1 | | 1/1998 |
| GB | 1033708 | | 11/1966 |

* cited by examiner

*Primary Examiner*—Michael H. Thaler
(74) *Attorney, Agent, or Firm*—St. Onge Steward Johnston & Reens LLC

(57) ABSTRACT

What is described here is an instrument for application in endoscopic surgery, comprising a shaft (10)

including two forceps elements at its distal end which are operable independently of each other by operating elements (17), whereof one is pivotable about an axis at least approximately orthogonal on the longitudinal axis of the instrument and including at least one continuous passage (12) between the jaws of said two forceps elements.

The inventive instrument is characterised by the provisions that the other forceps element is not pivotable, and that the pivotable jaw element or elements (16) of each forceps element are pivotable about axes (16a) which are each arranged approximately in parallel with the connecting line between the seizing regions of said forceps elements.

18 Claims, 1 Drawing Sheet

INSTRUMENT FOR APPLICATION IN ENDOSCOPIC SURGERY

This is a continuation of International Application PCT/DE99/00057 filed Jan. 14, 1999 and DE 198 00 917.8 filed Jan. 14, 1998.

DESCRIPTION

1 Field of the Invention

The present invention relates to an instrument for application in endoscopic surgery.

2 Prior Art

An instrument which the wording of the introductory clause of Patent claim 1 starts out from is known from the German Patent De 43 24 254 C1.

That prior art reference discloses a surgical instrument for endoscopic operations which comprises a shaft. Three passages are provided in that shaft, which are disposed at the apices of an isosceles triangle. A pair of forceps or the like can be inserted into two of the passages, which present each a forceps jaw which can be pivoted. The third passage is provided for the insertion of an optical system.

The relative orientation of the forceps may be optional because the forceps may be inserted into the respective passage at any optional angle of rotation.

Even though the known surgical instrument can hence be adapted to almost any surgical operation for the performance of defined tasks which require precisely defined operating cycles, the expenditure for adjustment is very high:

In a number of endoscopic surgical operations it is necessary for instance, to "contract" two tissue parts which are separated from each other, to maintain them in this condition, and to joint them subsequently, e.g. by a suturing or adhesive operation.

One example of such type of surgery is the operation on torn ligaments in a joint, such as the knee joint, or the in-vitro fertilisation of the fallopian tubes. Another example is described in the article by D. J. Tibbs et al., "Arterial Replacement with Minimal Interruption of Blood Flow", published in "The Lancet", 1958, pp. 292 to 294.

With the instrument known from the German Patent DE 43 24 254 C1 it is not possible to perform these operations because the pivoting axes of the elements of the forceps jaw and of the forceps jaw are disposed in parallel with each other. Hence the two bendable forceps, which are introduced independently of each other into a shaft with a plurality of passages, do not permit a coordinated movement in the sense of a selective approach of parts held by the two jaws of the forceps. Moreover, the individual passages are disposed at the apices of an isosceles triangle so that the manipulation of the contracted tissue part by means of an instrument introduced into the third passage is rendered more difficult.

With conventional—separate—instruments such operations require not only much time but also a high degree of manual skill from the physician performing the operation because the latter is bound to handle several instruments, which are separately introduced into the human body, and to co-ordinate their movements.

BRIEF DESCRIPTION OF THE INVENTION

The present invention is based on the problem of providing an instrument for application in endoscopic surgery which facilitates, for instance, the operations of "contracting" two tissue parts separated from each other, maintaining the tissue parts in the contracted condition, and manipulating them subsequently, e. g. their joining by a suturing or adhesive operation. The inventive instrument is moreover intended to have a simple structure and to require only a slight expenditure in terms of preparation and adjustment.

The present invention starts out from an instrument for application in endoscopic surgery, which comprises a shaft including two forceps elements on its distal end, which are operable independently of each other by operating elements, with one of said forceps elements being pivotable about an axis at least approximately orthogonal on the longitudinal axis of the instrument and/or displaceable in a direction orthogonal on the longitudinal axis of the instruments, and which comprises at least one further passage.

In order to avoid incorrect operations the possibilities of manipulation are restricted on the inventive instruments for the movements of the forceps jaws as one unit:

In one embodiment merely one set of forceps jaw elements is pivotable whilst the other set of forceps element is not pivotable.

In the embodiment defined in claim 1 the other forceps element is pivotable about an axis which is not parallel with the pivoting axis of the first forceps element or displaceable in a direction orthogonal on the longitudinal axis of the instrument.

The inventive instrument so configured is suitable particularly for the performance of special tasks such as the contraction of tissue parts.

To this end it is preferable to design the pivotable part(s) of the jaw of each forceps element for pivoting about axes whereof each is arranged at least approximately in parallel with the connecting line between the seizing regions of the forceps elements. This orientation, which is opposite to the orientation between the forceps jaw and the pivoting axis as known from the German Patent DE 43 24 254 C1, permits the contraction even of sensitive tissue parts because the jaw parts, in the seizing operation, move approximately orthogonally on the direction in which the tissue parts are moved by pivoting the forceps elements.

When the distal exit aperture of a continuous passage is disposed between the jaws of the two forceps elements and when the continuous passage is so configured that a surgical instrument can be inserted (inter alia) into this passage, which instrument co-operates with the jaws of the two forceps elements, the following mode of operation is conceivable, for instance, for joining separate tissue parts:

The inventive instrument is introduced into the cavity where the tissue parts to be joined are located. The free ends of the tissue parts, i.e. the fallopian tubes, for instance, are seized with the jaw of one respective forceps element. Then the forceps jaw of one pair of forceps is moved in a direction orthogonal on the longitudinal axis of the instrument towards the other pair of forceps. With the two forceps elements of the instrument seizing the tissue parts, the first free end of one of the two tissue parts to be joined is moved towards the end of the other tissue parts. As soon as the free ends have reached a position in which it is possible to perform the joining operation the operating physician carries through the joining step. During the joining operation and possibly even after this step the parts to be joined are held with the inventive instrument.

It is, of course, possible to use the inventive instrument also for other treating or processing operations in the human or animal body or in engineering applications.

It is moreover expedient to provide a pivoting operating element on the proximal end of the instrument for each pivotable forceps element, which when operated varies the pivoting angle and hence the spacing between the forceps elements in the direction of the transverse axis. The variation of the pivoting angle does not take any influence on the position of the jaw parts of this forceps element relative to each other. It is thus possible to move the free tissue parts to be joined towards each other precisely and without any damage to the tissue.

Furthermore an improvement is conceivable wherein the forceps elements are structured in the manner of known forceps or are known forceps, respectively, which are inserted into a shaft as a single unit. This configuration simplifies both the manufacture, the storage operations at the manufacturer, and the cleaning of the inventive instrument.

It is furthermore expedient to configure the shaft in the manner of a trocar or a laparoscope known per se. This trocar shaft may have an outside diameter of 10 mm to 13 mm, for instance when fallopian tubes are to be sutured.

It is moreover preferable to provide the elements for operating the jaw parts of the forceps in the form of handle parts—such as scissors handles, forceps handles or the like—which are biased into the position in which the respective forceps jaw is closed. This configuration has the advantage that the physician need not hold the jaw parts of the two forceps by holding the handles in a closed condition when contracting the tissue parts.

The spacing between the two forceps elements can fundamentally be varied in the most different ways. It is possible, for instance, to hold at least one forceps element on a resilient and outwardly bent mount. Then the forceps element is "pressed inwardly" or the point of articulation is shifted, respectively, by means of a linear guide or a sleeve.

A particularly wide range of adjustment is achieved—specifically in view of the restricted diameter of endoscopes—including various possibilities of pivoting the distal end of the forceps elements or forceps, respectively, as a single unit:

The forceps jaws may be a component of flexible forceps known per se which have distal ends which are equally bendable in a manner known per se.

The pivoting or bending movement of the forceps jaws can be provoked in the most different ways:

Transmitting elements such as Bowden controls, connecting or tie rods may be provided which transmit the movement of the operating elements to the forceps jaws. It is furthermore possible that distally disposed actuators are provided which create the pivoting or bending movement. The actuators may be electrically operable micro actuators such as micro motors in particular.

It is furthermore possible to use at least one rigid pair of forceps as forceps which has a distal end adapted to be bent as a single unit and having jaw parts which are connected via a rod or the like to a proximally disposed operating element. A pair of forceps of this type is described, for instance, in the document WO 97/49342.

It is preferable to provide an equalising mechanism which prevents a variation of the relative angular position of the two jaw parts of the jaw when the distal end is bent or pivoted, respectively, as a single unit, because in such a case the tissue can neither be damaged nor slide out of the respective jaw parts when the spacing of the two forceps is varied.

In the event of application of a pair of rigid forceps it is furthermore preferable to configure the rod, in a manner known per se, for flexibility in the bending region or for closing the jaw in response to traction or pressure.

In the event of application of "rigid forceps" it is moreover preferable to provide an actuator and specifically a regulating screw which may be operated in a way that the distal end is bendable or pivotable, respectively.

The regulating screw may be disposed at an angle of 90° relative to the longitudinal axis of the instrument or concentrically with the longitudinal axis of the instrument.

The handling of the inventive instrument is further facilitated if certain angular positions of the two pairs of forceps are indexed or when the regulating screw presents a catch at defined angular positions.

The most different instruments can be inserted into the additional passage:

It is possible, for instance, to insert a suturing means or a strapping means.

Specifically when distal and proximal fallopian tube remnants are to be joined with each other after the introduction of a catheter it is expedient to provide the strapping means in the form of a catheter which permits the application of a fibrinous adhesive.

The forceps jaws of the inventive instrument may be designed fundamentally in any known configuration:

It is particularly advantageous, however, to form the forceps jaws by two respective seizing jaws. These seizing jaws may be provided with teeth so that the respective tissue parts may be securely seized.

In such a design the shape of the seizing jaws may be matched with the tissue parts to be joined so that a large-area positive clamping will be achieved.

The adaptation to different operating conditions is facilitated by the provision that the forceps jaws are additionally displaceable along the direction of the longitudinal axis of the instrument relative to the instrument body. In this design each forceps jaw may be shifted independently of the other forceps jaw.

Due to the displaceability along the direction of the longitudinal axis it is possible, inter alia, to compensate the angular offset which is produced as a result of the pivoting motion. If necessary it is also possible to provide a restricted guidance for compensation of the angular offset.

DESCRIPTION OF THE EMBODIMENT

Figure 1:
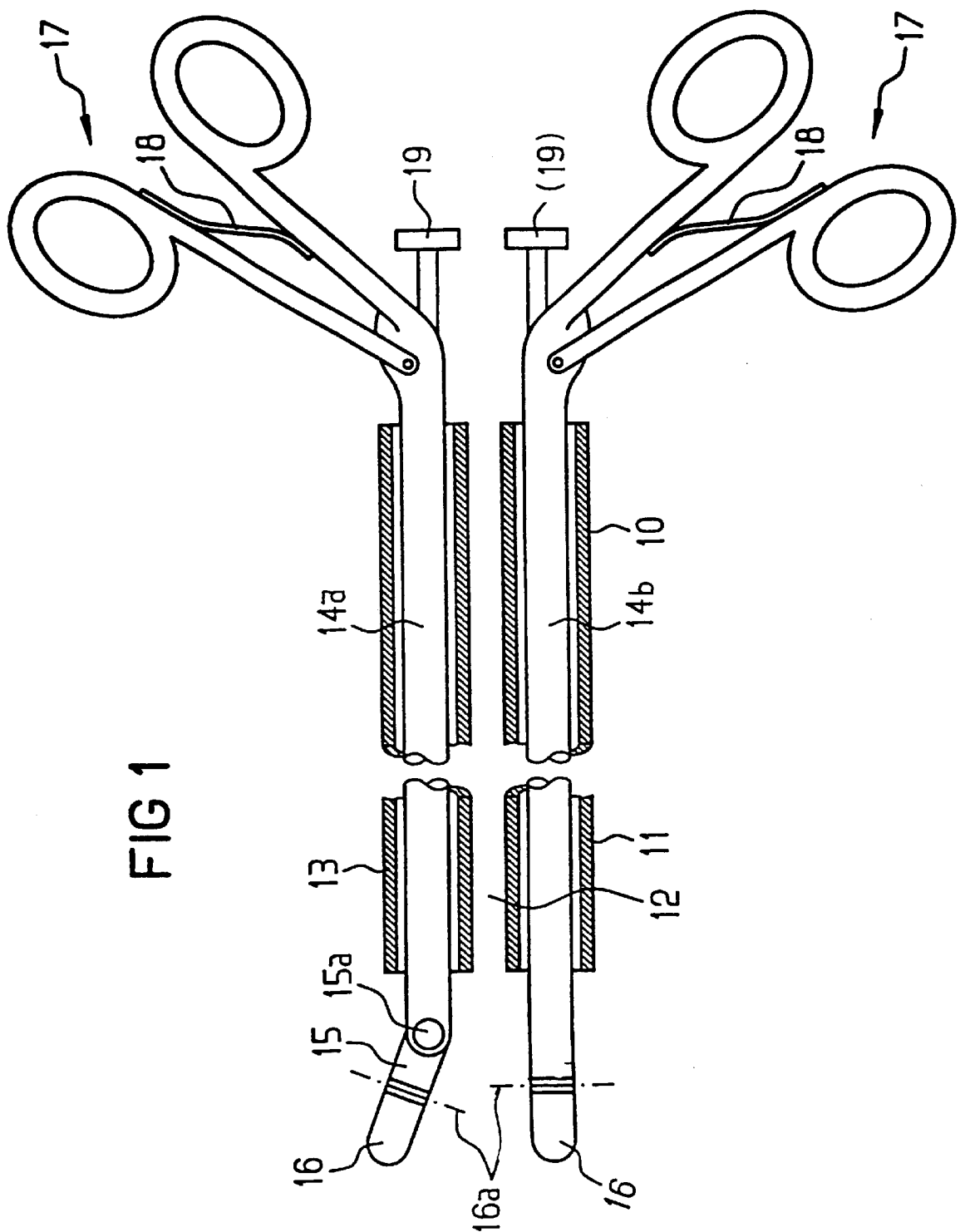
FIG. 1 is a partly sectional side view of one embodiment of an inventive instrument.

FIG. 1 shows one embodiment of the invention. This instrument comprises a shaft 10 in which three passages 11 to 13 are provided in a side-by-side relationship. One respective pair of forceps 14a or 14b is inserted into each of the two outer passages. The distal end 15 of the forceps 14a is pivotable as a single unit about a pivoting axis 15a. The distal end 15 of the forceps 14b may be rigid. In an alternative the distal end of the forceps 14b may be pivotable about an axis which is not parallel with the pivoting axis 15a of the forceps 14a or displaceable in a direction orthogonal on the longitudinal axis of the instrument.

The distal end 15 of both pairs of forceps moreover comprises jaw elements 16 of the two pairs of forceps; the jaw elements 16 are pivotable about an axis 16a which is orthogonal on the axis 15a (in the plan view of FIG. 1 merely one of the two jaw elements can be seen).

Scissors handles 17 are provided in a manner known per se for operation of the jaw elements, which are biased by a spring 18 into the position in which the jaw elements 16 are closed. For bending the distal end 15 of the pair of forceps 14a as a single unit an operating element 19 is provided which is arranged coaxially with the longitudinal forceps axis. If the distal end 15 of the forceps 14b, too, is pivotable about an axis not parallel with the axis 15a this pair of forceps comprises an operating element 19, too.

The operating elements 17 and 19 are connected to the respective distal elements via rods or bowden controls.

Each operating element 19 preferably presents an indexing or catch means so that defined bends of the elements 15 can be easily set.

In addition, the forceps 14 are displaceable in their respective passages along the direction of their longitudinal axes so that extensive manipulations are possible.

The shape of the seizing jaws, which are provided with teeth in particular, is matched whit the respective application.

An instrument such as a catheter for an adhesive, a suturing means or also another pair of forceps can be inserted into the central passage 12.

On account of the inventive configuration it is possible to perform the most different operations whitout any risk of demanding too much from the operator as a result of excessive possibilities of adjustment.

What is claimed is:

1. Instrument for application in endoscopic surgery comprising a shaft; two pairs of forceps jaws at a distal end of the shaft which are operable independently of each other by operating elements, one of said pairs of forceps jaws pivotable about an axis at least approximately orthogonal to a plane containing a longitudinal axis of the instrument and a space separating said two pairs of forceps jaws, characterized in that the other of said two pairs of forceps jaws is not pivotable, and that at least on jaw of each pair of forceps jaws is oriented to be pivotable about and axis which is approximately parallel.

2. Instrument according to claim 1, characterized in that a pivoting operating element is provided on the proximal end of the instrument for the pivotable pair of forceps jaws, which when operated varies the pivoting position of the pivotable pair of forceps jaws without any variation of the position of the pivotable pair of forceps jaws relative to each other.

3. Instrument according to claim 1, characterized in that each of said two pairs of forceps jaws are components of one respective pair of forceps which is inserted as a single unit into a passage of said shaft.

4. Instrument according to claim 3, characterized in that said forceps are displaceable in the respective passage in the direction of the longitudinal axis of said shaft.

5. Instrument according to claim 4, characterized in that operating elements for the jaw elements of said forceps which are proximal handle pieces biased into the position in which the forceps jaw elements are closed are provided.

6. Instrument according to claim 1, characterized in that transmitting elements are provided which create a pivoting movement of the pivotable pair of forceps jaws.

7. Instrument according to claim 6, characterized in that an actuator is provided which creates the pivoting movement of the pivotable pair of forceps jaws.

8. Instrument according to claim 1, characterized in that defined angular positions of the pivotable pair of forceps jaws are indexed.

9. Instrument according to claim 1, characterized in that the instrument is adapted for being inserted into a trocar shaft.

10. Instrument according to claim 9, characterized in that said trocar shaft has an outside diameter of 10 to 13 mm.

11. Instrument according to claim 1, characterized in that a joining means is insertable into said space.

12. Instrument according to claim 11, characterized in that said joining means is a catheter permitting the application of a fibrinous adhesive.

13. Instrument according to claim 1, characterized in that the jaws of each pair of forceps jaws are formed by two seizing or scissors jaws.

14. Instrument according to claim 13, characterized in that said seizing jaws are provided with teeth.

15. Instrument according to claim 13, characterized in that the shape of said seizing jaws is matched with tissue parts to be joined.

16. Instrument according to claim 1, characterized in that the jaw of said two pairs of forceps jaws are additionally displaceable along the direction of the longitudinal instrument axis.

17. Instrument according to claim 16, characterized in that each forceps jaw element is displaceable independently of the other forceps jaw element.

18. Instrument for application in endoscopic surgery, comprising:

an endoscope shaft having an inner passage for insertion of a surgical manipulating means, and two forceps passages of which one is disposed on each side of said inner passage, said inner passage and said forceps passages each having a longitudinal axis and each passing through said shaft in a longitudinal direction; and first and second forceps, each passing through one of said forceps passages, respectively, and having an operating element at a proximal end outside one of said forceps passage and a set of two jaws at a distal end outside one of said forceps passage, said first and second forceps being operable independently of each other;

wherein the set of jaws of said first forceps is pivotally supported as a unit on a pivot axis approximately orthogonal to a plane containing the longitudinal axes of said two forceps passages;

the set of jaws of said second forceps is not pivotally supported as a unit; and at least one of the two jaws of each set of jaws is pivotally supported to perform a pivotal movement with respect to the other jaw about an axis parallel to said plane containing the longitudinal axes of said forceps passages so as to open or close the jaws.

* * * * *